United States Patent [19]

Annino et al.

[11] Patent Number: 4,496,433

[45] Date of Patent: Jan. 29, 1985

[54] APPARATUS AND METHOD FOR DETERMINING THE AMOUNT OF A SAMPLE GAS COMPONENT

[75] Inventors: Raymond Annino, North Smithfield, R.I.; Maynard C. Cheney, Norfolk; Kenneth S. Fletcher, Rehoboth, both of Mass.

[73] Assignee: The Foxboro Company, Foxboro, Mass.

[21] Appl. No.: 566,345

[22] Filed: Dec. 28, 1983

[51] Int. Cl.³ .................. G01N 27/58; G01N 31/08
[52] U.S. Cl. .................. 204/1 T; 73/23.1; 204/406; 204/410; 204/412; 204/425
[58] Field of Search .......... 204/1 S, 1 K, 406, 410, 204/412, 425; 73/23.1

[56] References Cited

U.S. PATENT DOCUMENTS 3,860,498  1/1975  Jones .................. 204/1 T

FOREIGN PATENT DOCUMENTS 37801  5/1965  German Democratic Rep. .................. 204/410

Primary Examiner—G. L. Kaplan
Attorney, Agent, or Firm—Parmelee, Bollinger & Bramblett

[57] ABSTRACT

A gas chromatograph for measuring the amounts of selected sample gas components such as oxygen and carbon monoxide. The system comprises a high-temperature (600° C.) zirconia cell detector supplied on one side with a continuous stream of oxygen flowing at a constant rate. A voltage source connected to the zirconia cell transports all of this oxygen to the other side of the cell, resulting in a constant background cell current. Sample components from the chromatographic column are injected sequentially into the oxygen stream. When oxygen is injected the cell current increases due to the increase in total oxygen available for transport through the cell. When carbon monoxide is injected, it is fully combusted with the oxygen, and the current correspondingly decreases due to reduction of the oxygen available for transport. The deviation in cell current with reference to the background current is integrated for each component to produce output signals indicating the amount of the component.

24 Claims, 5 Drawing Figures

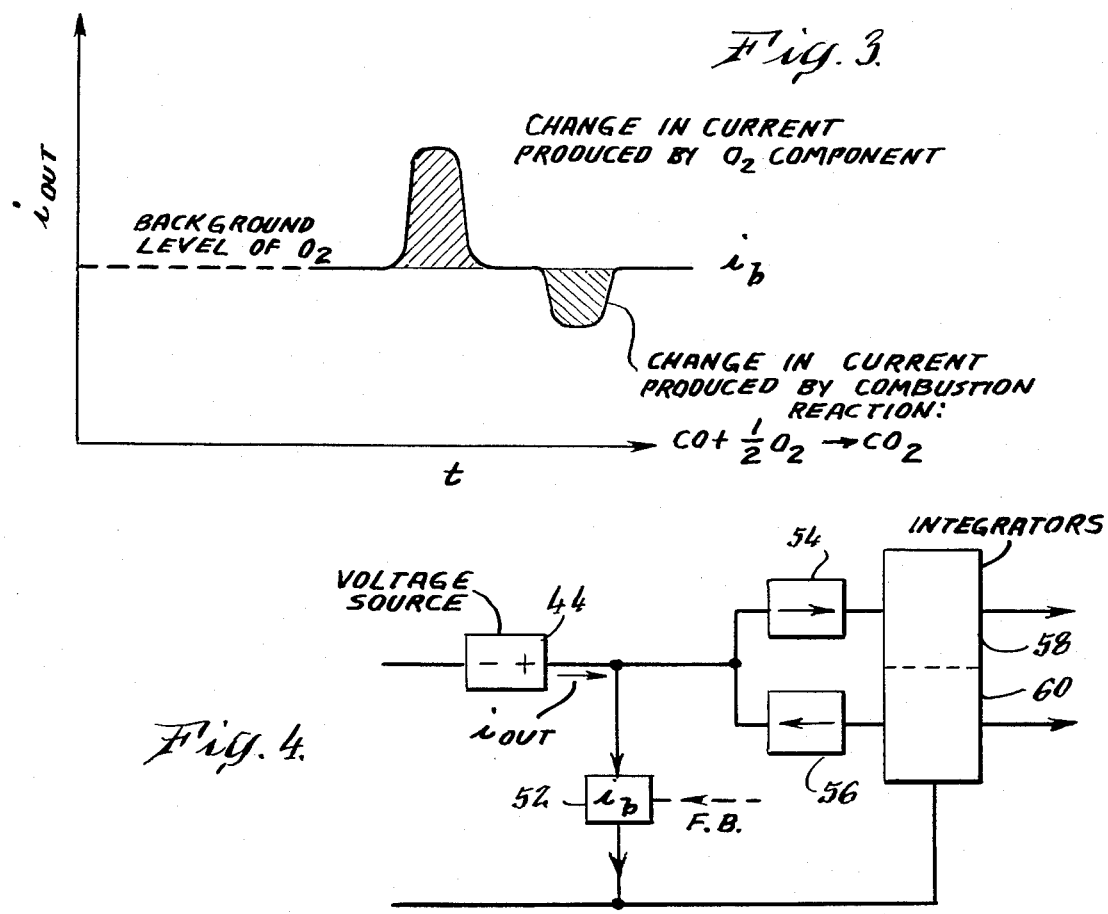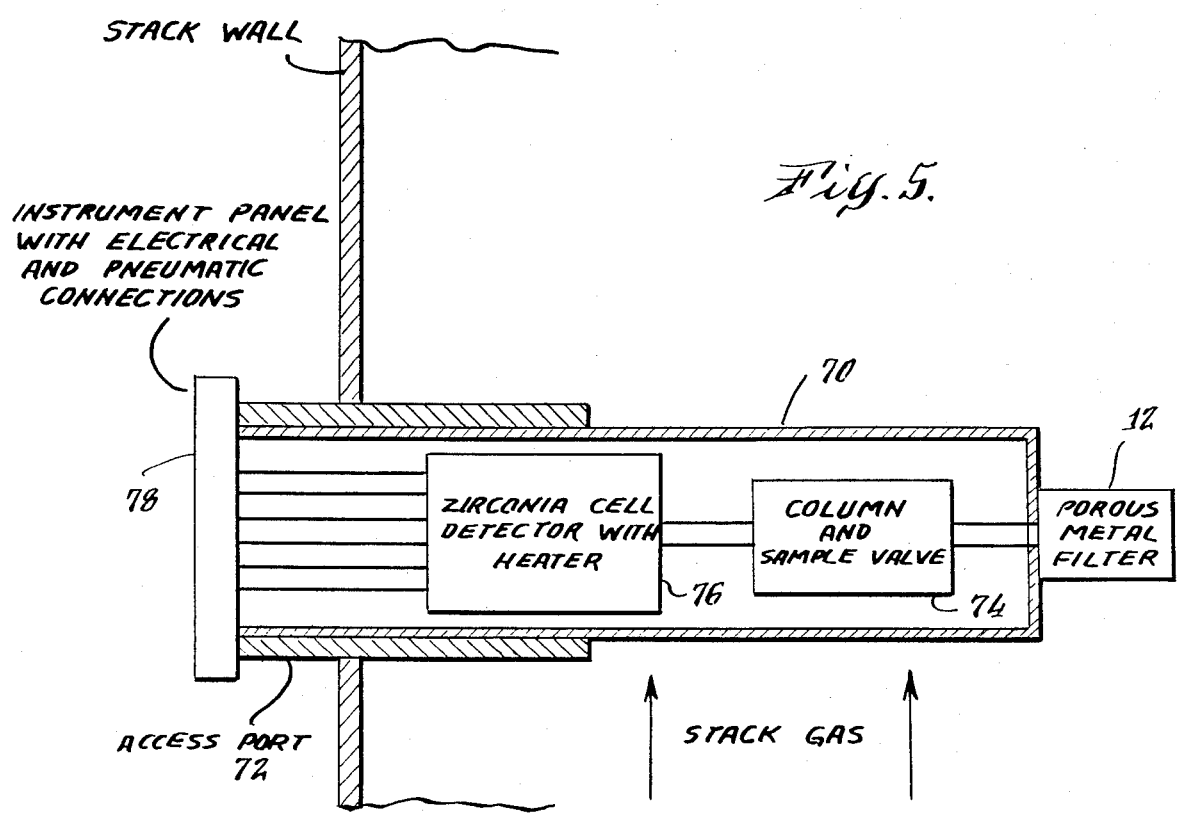

APPARATUS AND METHOD FOR DETERMINING THE AMOUNT OF A SAMPLE GAS COMPONENT

BACKGROUND OF THE INVENTION

1. Field of the Invention

This invention relates to methods and apparatus for determining the amounts of one or more selected components of a gas sample. More particularly, this invention relates to measurement apparatus capable of providing accurate quantitative results and that does not require detector calibration with known standards.

2. Description of the Prior Art

A wide variety of procedures have been developed over the years for measuring the amount (i.e. weight) of a selected component of a gas sample. One technique that has proven highly successful is gas chromatography, wherein a predetermined quantity of gas sample containing multiple components is passed through a separation column. Such a column, as by means of selective adsorption chracteristics, separates the components of the sample so that they elute sequentially to permit measurement of each component in turn.

Many different detectors have been employed to measure the amount of the components as they elute from the column. A common characteristic of all conventional detectors is that they require calibration in order to achieve accurate quantitative results. Moreover, no available detector is very sensitive to carbon monoxide, a gas often of practical interest in certain process industries. For example, it is desirable to be able to determine rapidly and efficiently both the oxygen and the carbon monoxide content of the stack gas from gas, oil or coal-fired furnaces and boilers.

SUMMARY OF THE INVENTION

In a presently preferred embodiment of the invention, to be described hereinbelow in detail, there is provided a novel method and apparatus for measuring the amount of oxygen and carbon monoxide in a gas sample. However, it will be understood that the techniques of the invention may be used for making measurements of many other gas components. The measurement apparatus and methods described herein are uniquely advantageous when forming part of a gas chromatography system.

The types of devices employed in the disclosed system are not individually new, but are used in a new way to create a significantly improved result. The principal measurement device used in the system is an oxygen-responsive cell comprising an oxygen-ion-conductive solid electrolyte. Typically such electrolyte is a metal oxide; the specific electrolyte used in the cell disclosed herein comprises stabilized zirconium oxide heated to a very high temperature, e.g. 600° C. or above. Such a "zirconia cell" presently is considered to be the best of the oxygen-ion-conductive cells for use in this invention.

In the apparatus to be described hereinbelow, a zirconia measurement cell is supplied on one side with a continuous stream of an inert carrier gas carrying a fixed concentration of oxygen and flowing at a fixed rate. The cell is energized with a source of electrical current having sufficient capacity to transport all of the oxygen on that one side to the other side. That is, the oxygen on that one side of the cell is fully exhausted by transference to the other side of the cell.

In this ion-conduction process, the transport of each oxygen molecule requires that exactly four electrons be supplied by the source of electrical current. Therefore, when the cell receives oxygen at a constant rate, the electrical current supplied to the cell similarly will be constant. Such constant current is referred to hereinbelow as the "background" current level.

The gas components to be measured are injected sequentially into the stream of oxygen supplied to the zirconia cell as described above. In the chromatographic system disclosed, oxygen is the first component to arrive from the separation column, and augments the continuous stream of oxygen being fed to the cell so as to increase momentarily the amount of oxygen available at the cell wall. Since all of the oxygen, including that from the chromatographic column, will be transported through the cell, there will be an increase in the cell current corresponding to the added oxygen from the chromatographic column. This increase in electrical current is integrated (by known means), and the result of the integration provides an exact coulometric measure of the weight of the oxygen component received from the chromatographic column.

The next gas component to elute from the chromatographic column in the described system is carbon monoxide. Because the zirconia cell operates at a very high temperature (600° C. or higher), the carbon monoxide component will be fully combusted with the oxygen of the constant-rate stream flowing to the cell. This combustion will reduce the amount of oxygen presented to the cell, and thus will reduce correspondingly the electrical current required to transport oxygen through the cell. This reduction in electrical current is integrated, and the result of the integration provides an exact coulometric measure of the weight of the carbon monoxide component supplied to the zirconia cell.

It may particularly be noted that no calibration of the apparatus is needed. This is because the weight measurement in each case is a function solely of the number of coulombs of electrical charge needed to effect transport of the oxygen through the cell. Assuming that the stoichiometry of the combustion reaction is known (that is, the difference in coulombs of charge resulting from the background current flowing through the detector for the time interval of the current peak and that resulting during the current peak), the integral of the deviation in current (i.e. the difference between the measured current and the background current) will in each case provide an exact measure of the weight of the gas component of the sample. It further may be noted that the measurements made as described herein are not subject to errors due to the effects of temperature on the zirconia cell characteristics, since the results are dependent only on the number of coulombs required to transport the oxygen through the cell. That number does not change with temperature, and its measurement is not dependent upon temperature.

Other objects, aspects and advantages of the invention will in part be pointed out in and in part apparent from the following description considered together with the accompanying drawings.

BRIEF DESCRIPTION OF THE DRAWINGS

FIG. 3 is a graph showing how the output of the zirconia cell detector of FIG. 2 varies with time when supplied sequentially with oxygen and carbon monoxide;

FIG. 4 is a schematic diagram showing electronic circuitry for integrating measurement signals produced by oxygen and carbon monoxide; and FIG. 5 illustrates schematically the constructional arrangement of a stack gas analyzer based on the present invention.

DETAILED DESCRIPTION OF A PREFERRED EMBODIMENT

Figure 1:
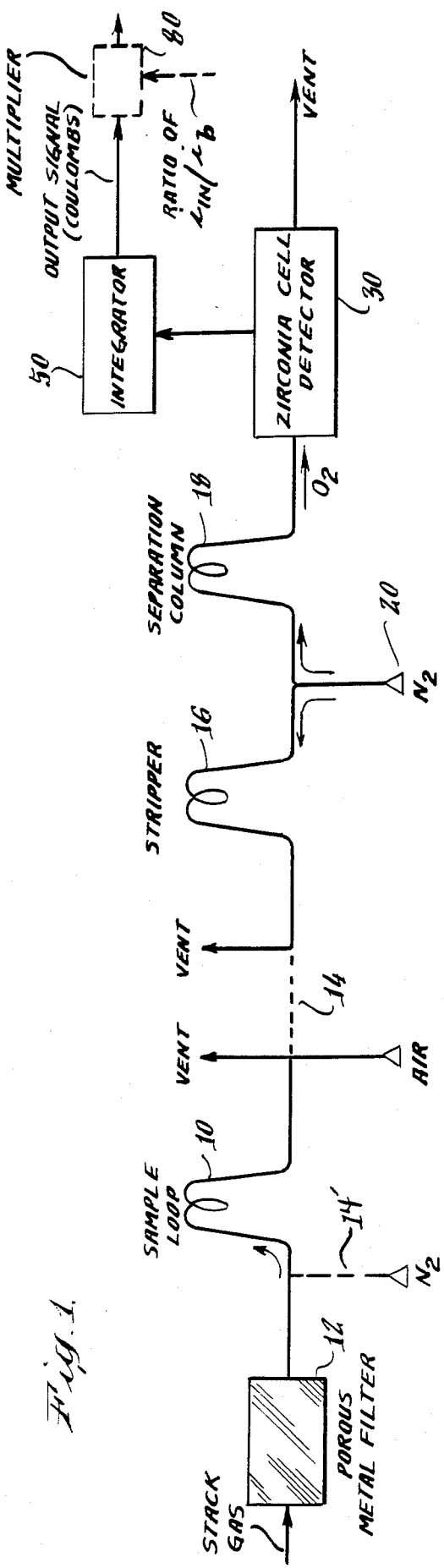
FIG. 1 shows diagrammatically a gas chromatograph generally of known configuration but having a detector employing a zirconia cell.

Referring first to FIG. 1, there is illustrated a gas chromatography system in accordance with the present invention, and particularly adapted for use as a stack gas analyzer. The apparatus includes a sample loop 10 to receive stack gas through a porous metal filter 12. Any convenient means can be used for forcing the gas into the loop, e.g. as by means of an aspirator coupled to a pneumatic air source, as shown.

After the sample loop is filled with gas, it is coupled, as by means of a conventional pneumatically-operated sample valve schematically shown with a dotted line link 14, to the chromatographic column elements and by link 14' to carrier gas whose function is to carry the sample out of the loop into the chromatographic columns. Such elements in this case comprise a stripper 16 and a separation column 18. When the desired sample components have reached the separation column, the sample valve is shifted back to its original state (with link 14 and 14' interrupted). Nitrogen from a source 20 thereupon backflushes the stripper 16, and at the same time serves as a carrier to force the sample component through the column 18 and into the zirconia cell detector 30.

Figure 2:
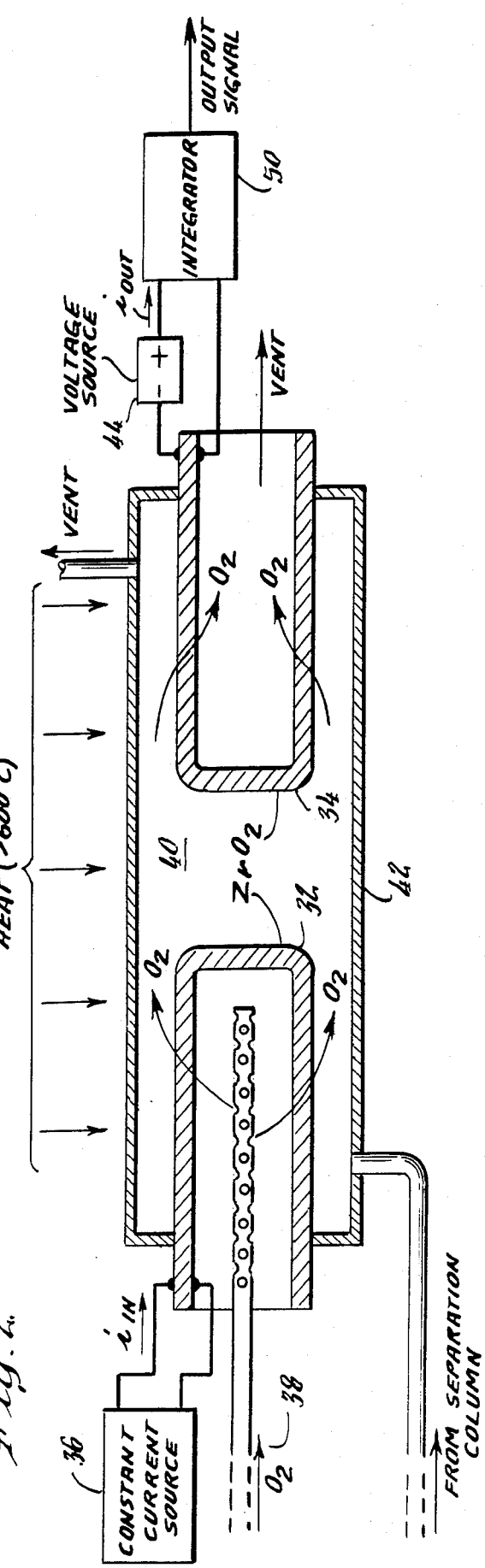
FIG. 2 is a diagram illustrating the construction of a zirconia cell detector as used in the FIG. 1 system.

Referring now to FIG. 2, the detector 30 comprises two zirconia cells 32, 34 each of tubular, closed-end form. The left-hand cell 32 serves as an oxygen pump, to produce a continuous stream of oxygen at a fixed, predetermined flow rate. For this purpose, a source of constant current 36 is connected to conventional electrodes (not shown) on the inner and outer surfaces of the zirconium oxide of the cell 32, and a source of oxygen is connected to a tube 38 leading to the interior of the cell. With constant electrical current flowing to the zirconia cell electrodes, a correspondingly constant flow of oxygen ions will be transported through the cell wall to the outer surfaces of the cell.

Both of the zirconia cells 32, 34 are contained within a closed chamber 40 formed by a cylindrical housing 42 which is sealingly secured to the ends of both cells. Thus, the continuous stream of oxygen generated by the pump cell 32 is supplied to the outer surfaces of the right-hand cell 34, which serves as a measurement cell. Heating elements (not shown) are provided outside of the chamber 40 to maintain the temperature of both cells 32, 34 at least at 600° C.

The measurement cell 34 is supplied with electrical current by a voltage source 44 connected to the cell electrodes (not shown) on the inner and outer surfaces of the cell. This voltage source is designed to provide sufficient current to transport through the cell wall all of the oxygen available at the outer cell surface, with insignificant delay. The oxygen which is transported through the cell exits through a vent. The magnitude of current flow ($i_{out}$) from the source 44 required to transport all of the oxygen supplied by the pump cell 32 will be constant, and is referred to herein as the background current.

The oxygen ($O_2$) and carbon monoxide (CO) in the stack gas sample will be separated in known fashion by the column 18, typically in less than one minute. The oxygen will elute first from the column into the chamber 40, and increase the oxygen content in that chamber correspondingly. This in turn will increase the output current $i_{out}$ from the voltage source 44 needed to transport oxygen through the cell 34.

The difference between the background current level and the increased level of current due to the sample oxygen component (see FIG. 3) is summed as a function of time by an integrator 50. Such integration produces a coulometric measure of the total amount of added oxygen (i.e., oxygen which is in addition to the background level of oxygen) transported through the zirconia cell 34. This integrated result is developed as an output signal from the integrator, representing the weight of the oxygen component of the stack gas sample.

When the CO component subsequently elutes from the column 18 into the chamber 40, it will be fully combusted with a stoichiometric quantity of the background oxygen already present in that chamber, as a consequence of the very high temperatures within the chamber. This will cause the output current $i_{out}$ to correspondingly decrease below the background level of current, as shown in FIG. 3. The integrator 50 integrates this deviation in current to produce a corresponding output signal. This signal will represent coulometrically the weight of the CO which was in the gas sample, since the combustion reaction $CO + \frac{1}{2}O_2 \rightarrow CO_2$ requires that the amount of oxygen consumed in combustion will correspond exactly to the amount of CO in the sample.

The integration operations described above can be performed by conventional means, using techniques which are well known in the art of chromatography and sample component measurement. For example, Annino et al U.S. Pat. No. 3,717,028 discloses chromatographic apparatus with integration means including timing and other controls. The deviation signal which is integrated in the present disclosure can be produced in accordance with straight-forward known electronic techniques. For example, as shown in FIG. 4, a current source 52 can be connected to the $i_{out}$ line to null out the background current $i_b$, in order to obtain the deviation current for integration. The magnitude of the current from the source 52 can if desired be controlled automatically to null by a feedback signal developed in known fashion. The positive-going signal of the oxygen component can be discriminated from the negative-going signal of the CO component with known electronics of simple construction. FIG. 4 illustrates such discriminating circuits 54, 56 which can basically comprise unidirectional current elements such as conventional diodes, connected for oppositely-directed current flows as indicated by the arrows. The integrator 50 can be provided as two separate integrators 58, 60 for the two current deviation signals, respectively, to produce two corresponding output signals for the oxygen and carbon monoxide measurements.

FIG. 5 illustrates the structural arrangement of a stack gas analyzer in accordance with the present invention. The analyzer apparatus comprises an elongate outer protective shell 70 which extends through an access port 72 in the stack wall. The porous metal filter 12 is at the end of the shell 70, and is connected to the chromatographic apparatus 74 including a separation column and sample valve with associated controls. The output of the separation column is directed to the zirconia cell detector 76 which preferably is constructed as shown in FIG. 2. The output signals from the integrator of this detector may be displayed on an instrument panel 78 which may have other data displays and operating controls as appropriate to the functioning of the apparatus.

An additional advantage of the disclosed measurement system is that it provides for ready self-diagnosis of possible errors such as due to drift in the detector cell or the oxygen pump portion of the system. When the system is operating properly in the manner disclosed hereinabove, the pump current $i_{in}$ will be equal to the background output current $i_b$ of the detector. Component drift would produce an inequality which can be detected by known comparator means, comparing the value of $i_{in}$ with the background current $i_b$. Detection of such inequality could serve to activate an alarm, to indicate that corrective measures are needed. Alternatively, the ratio of $i_{in}$ to $i_b$ could be employed as a correction factor to proportionately adjust the value of the final output signal from the integrator, thus compensating for drift and assuring a correct output signal. This could for example be achieved by directing the integrator output signal to a conventional electronic multiplier 80 (see FIG. 1) having a multiplication factor controlled in known fashion to correspond inversely to the ratio of $i_{in}$ to $i_b$, and using the multiplier output as the final corrected output signal.

Although a specific preferred embodiment of this invention has been described hereinabove in detail, it is desired to emphasize that this has been for the purpose of illustrating the invention, and should not be considered as necessarily limitative of the invention, it being understood that many modifications can be made by those skilled in the art while still practicing the invention claimed herein.

What is claimed is:

1. An instrument for determining the amount of a selected gas component in a sample, comprising:
   a solid-electrolyte oxygen-sensor cell;
   means to furnish a continuous stream of oxygen at a fixed rate to the region adjacent one side of said cell;
   voltage supply means coupled to said cell to develop a potential thereacross for transporting through said cell all of the oxygen present at said one side whereby the cell current normally is at a constant background level corresponding to said fixed rate of oxygen supply;
   means to combine said selected gas component with said continuous stream of oxygen, so as to alter for a period of time the amount of oxygen available for transport through said cell; and
   means responsive to the cell current for integrating the deviation in current from said constant background level during said period of time, whereby the amount of said selected gas component may be determined by coulometric measurement effected by such integration.

2. Apparatus as claimed in claim 1, wherein said oxygen-sensor cell comprises a zirconia cell.

3. Apparatus as claimed in claim 2, wherein said zirconia cell is maintained at a highly-elevated temperature; said selected gas component fully combusting with oxygen from such continuous stream, thereby to reduce correspondingly the amount of oxygen available for transport through said cell so that the integral of the deviation in current from said background provides a precise, calibrated measure of the amount of said gas component.

4. Apparatus as claimed in claim 3, wherein said gas component includes carbon as one of its elements.

5. Apparatus as claimed in claim 4, wherein said gas component is carbon monoxide.

6. Apparatus as claimed in claim 5, wherein said instrument is supplied with an oxygen component in addition to said carbon monoxide component.

7. Apparatus as claimed in claim 1, for determining the amounts of two gas components, one consisting of oxygen and the other being a component which combusts with said continuous stream of oxygen;
   said oxygen component serving to increase the total amount of oxygen transported through said cell, to increase proportionately the level of cell current above said background level correspondingly;
   the combustion of said other component serving to reduce the amount of oxygen transported through said cell, to decrease proportionately the level of cell current below said background current;
   said current-responsive means comprising means for discriminating between a current increase and a current decrease with reference to said background current level.

8. Apparatus as claimed in claim 1, wherein said instrument forms part of a package supported within the stack of a boiler to monitor the stack gases;
   said package further including chromatographic separation means to furnish said instruments with separated components of the stack gas.

9. Apparatus as claimed in claim 1, wherein said means to furnish said continuous stream of oxygen comprises a second solid-electrolyte cell operable to produce oxygen at a rate proportional to a constant current fed thereto.

10. Apparatus as claimed in claim 9, including means responsive to the ratio of said constant current to said background current for producing a controllable function relating to the operation of said instrument.

11. Apparatus as claimed in claim 10, wherein said responsive means comprises means to automatically adjust the signal produced by said integrator so as to compensate for potential errors due to drift effects.

12. The method of determining the weight of a selected sample gas component, comprising the steps of:
   applying a continuous fixed-rate stream of oxygen to one side of a solid-electrolyte oxygen sensor cell;
   transporting all of the oxygen on said one side through said cell by the application to said cell of an electrical potential;
   sensing the background electrical current flow through said cell corresponding to said continuous stream of oxygen;
   combining said selected gas component with the oxygen of said continuous stream, thereby to produce an altered electrical current flow corresponding to changes in oxygen available for transport through said cell as said component combines with the oxygen of said continuous stream; and
   integrating the difference in current between said background current flow and said altered current flow to determine the weight of said component.

13. The method of claim 12, wherein said gas component is combined with said oxygen by combustion.

14. The method of claim 12, wherein said gas component is oxygen and merges with said stream of oxygen to augment the total amount of oxygen.

15. The method of claim 12, wherein the weights of two gas components are determined, one of said components being oxygen, comprising:
combining said two components with said stream of oxygen sequentially; and
discriminating between said two components in accordance with whether said current level increases or decreases from said background level.

16. The method of claim 15, wherein the other of said components includes carbon.

17. The method of claim 16, wherein said component including carbon is combined with said stream of oxygen by combustion.

18. Gas chromatographic apparatus comprising:
a separation column adapted to receive a gas sample and to elute the separate components of said sample in sequence;
a detector connected to the output of said column to receive said separated components after elution, said detector comprising:
a solid-electrolyte oxygen-sensor cell;
means to furnish a continuous stream of oxygen at a fixed rate to the region adjacent one side of said cell;
voltage supply means coupled to said cell to develop a potential thereacross for transporting through said cell all of the oxygen present at said one side whereby the cell current normally is at a constant background level corresponding to said fixed rate of oxygen supply;
means to direct said separated components from said column to said continuous stream of oxygen and to provide for the combining of said components with said oxygen so as to alter for a period of time for each said component the amount of oxygen available for transport through said cell; and
means responsive to the cell current during each such period of time for integrating the deviation in current from said constant background level, whereby the amount of each gas component may be determined by coulometric measurement effected by such integration.

19. Apparatus as claimed in claim 18, wherein at least one of said components comprises carbon.

20. Apparatus as claimed in claim 19, wherein one of said components is oxygen.

21. Apparatus as claimed in claim 20, wherein said detector includes means to discriminate between an increase and a decrease in current level, in order to distinguish the oxygen component appearing at the output of said column.

22. A stack gas analyzer comprising:
a protective outer shell arranged to extend through an access port in the stack to be monitored, and to be supported in that position;
a chromatographic separation column in said shell;
chromatographic sampling means in said shell for obtaining samples of the stack gas and directing said samples to the input end of said column;
a gas component detector comprising a solid-electrolyte oxygen-sensor measurement cell with one side thereof presented to a sealed chamber within said shell;
means coupling the output end of said column to said chamber;
means to supply oxygen to said chamber and to provide for combining such oxygen with at least one component of the gas sample;
means to supply oxygen to said chamber and to provide for combining such oxygen with at least one component of the gas sample;
a voltage source having positive and negative terminals connected respectively to the sides of said oxygen-sensor cell to provide a measurement current corresponding to the amount of oxygen transported through said cell; and
means responsive to said measurement current for producing an output signal representing the amount of said one sample component.

23. Apparatus as claimed in claim 22, wherein said responsive means includes an integrator connected to the circuit carrying said current flowing through said cell and arranged to produce said output signal.

24. A stack gas analyzer comprising:
a protective outer shell arranged to extend through an access port in the stack to be monitored, and to be supported in that position;
a chromatographic separation column in said shell;
chromatographic sampling means in said shell for obtaining samples of the stack gas and directing said samples to the input end of said column;
a gas component detector comprising a solid-electrolyte oxygen-sensor measurement cell with one side thereof presented to a sealed chamber within said shell;
means to supply oxygen at a fixed rate to said sealed chamber;
means coupling the output end of said column to said chamber;
electrical means for operating said oxygen-sensor cell to provide a measurement output signal representing the amount of one or more components of said gas samples;
said electrical means comprising a voltage source to transport all of the oxygen molecules from said sealed chamber to the other side of said cell, thereby to produce a current in an associated circuit; and
an integrator connected to the circuit carrying said current flowing through said cell;
said integrator including means to integrate the difference between the cell current corresponding to said fixed rate of oxygen supply and the cell current accompanying the elution of a gas component from said column.

* * * * *